(12) United States Patent
Kendell et al.

(10) Patent No.: US 6,364,738 B1
(45) Date of Patent: Apr. 2, 2002

(54) SOLITARY BEE NESTING BLOCK

(75) Inventors: Lamar C. Kendell, North Ogden; William Kemp; Jordi Bosch, both of Logan, all of UT (US)

(73) Assignee: The United States of America as respresented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/726,873

(22) Filed: Nov. 30, 2000

(51) Int. Cl.[7] .............................................. A01K 47/00
(52) U.S. Cl. .............................................. 449/29; 449/4
(58) Field of Search ........................... 449/3, 4, 20, 29, 449/30, 35

(56) References Cited

U.S. PATENT DOCUMENTS

| | | | | |
|---|---|---|---|---|
| 3,842,457 A | * | 10/1974 | Johnson | 449/11 |
| 4,199,832 A | * | 4/1980 | Glasscock et al. | 449/30 |
| 4,491,994 A | * | 1/1985 | Youssef | 449/4 |
| 4,765,007 A | | 8/1988 | McCarthy | |
| 5,618,220 A | * | 4/1997 | Mills | 449/4 |
| 5,738,922 A | * | 4/1998 | Kobayashi et al. | 428/36.5 |
| 6,010,390 A | | 1/2000 | Harper | |

OTHER PUBLICATIONS

J. Bosch et al., "Exceptional cherry production in an orchard pollinated with blue orchard bees", *Bee World* 80(4): 163–173 (1999).

H.A. Schuessler, "The Latest Buzz", *Frontier Magazine*, Sep.–Oct., pp. 21–23 (1998), published by Adventure Media, Seattle, Washington.

J. Jesiolowski, "get Bugs to Boost your Yield", *Organic Gardening*, May–Jun., pp. 28–33 (1996).

\* cited by examiner

*Primary Examiner*—Charles T. Jordan
*Assistant Examiner*—Elizabeth Shaw
(74) *Attorney, Agent, or Firm*—M. Howard Silverstein; Randall E. Deck; John D. Fado

(57) ABSTRACT

A nesting block for the rearing and management of cavity nesting solitary bees used for pollinating crops is disclosed. The nesting block includes a chamber having at least one substantially flat face, and a plurality of open tubes which extend therefrom into the chamber and which are closed at their opposite end. The chamber is formed from an organic polymeric material of which a major proportion thereof is polycarbonate.

40 Claims, 7 Drawing Sheets

SOLITARY BEE NESTING BLOCK

BACKGROUND OF THE INVENTION

1. Field of the Invention

The invention relates to improved nesting blocks for cavity nesting solitary pollinating bees and methods for rearing and managing such bees.

2. Description of the Prior Art

In the United States, honey bees have been typically looked upon as the only pollinator of our farm crops. Domestic hives of bees are rented and placed as needed to facilitate pollination. More than 2 million honey bee colonies are rented each year in the United States. Over $14 billion worth of crops nationwide rely upon pollination by insects, and of these, honey bees have carried the largest portion of the pollination work load. Most fresh fruit and vegetable, nut and seed crops rely upon insect pollination, including almonds, apples, blueberries, peaches, strawberries, cherries, melons, pears, plums, pumpkins and squash. Many seed crops also rely on insect pollination, including alfalfa, canola, sunflowers, carrots, and onions.

On most crops, honey bees can and do in fact provide an adequate job of pollinating. However, for some crops the honey bee provides only marginal pollination. This may be due to any of a variety of reasons including blooming patterns and blossom/flower anatomy. For instance, some crops bloom at lower temperatures and hence prior to the activity temperature of the honey bee. The blossoms and flowers of other plants may also have petal patterns which make it difficult for the honey bee to successfully pollinate that flower. In other situations, honey bees prefer to forage on other plants providing more abundant pollen or nectar than the target crop.

Of far greater concern however, has been the precipitous decline in the number of honey bees available for pollination. In the last 5 years, North American honey bees have come under unprecedented attack from 3 different sources. As a consequence, many beekeeping operations have been forced out of business, creating a critical shortage of honey bees for pollination in some areas. For example, in 1981, Pennsylvania had 85,000 commercial bee hives. By 1995, that number was reduced to 27,000 hives (Penn State Agriculture, Winter/Spring 1998). Other states have suffered similar losses, including Maine (80%), New Jersey (60%), New York (60–70%), Delaware (25–40%), Michigan (60%), and Wisconsin (67%). Wild honey bee populations have suffered as well. It has been estimated that the Northeast may have lost as many as 80% of its wild honey bees.

The causes for the bee colony losses have primarily been attributed to two parasites, tracheal mites and Varroa mites. Various treatments have been tried, and experiments with other methods and treatments are continuing in an effort to control these parasites. The results have been mixed and none are completely satisfactory. These parasites, compounded with poor weather and other mitigating factors, have left farmer and orchardist scrambling to find adequate pollinators for their crops.

To compound the problem with these mites, the Africanized honey bee (a cross between the European honey bee and African bees) has infiltrated Texas, New Mexico, Arizona, and California, and populations of these bees are steadily progressing Northward, bringing with them their hostile behavior and propensity for multiple stings. This has made it ever increasingly difficult to locate bee colonies for crop pollination in close proximity to populated areas.

Unfortunately, it has been the small to medium sized farm and farmers which have felt the pinch most severely. In this period of shortage, the suppliers of rented honey bee colonies have naturally catered to their larger accounts, and the smaller farms have been seriously in need of a pollinator for their crops. Moreover, it is often the small farmer who is found working the smaller pieces of ground located close to or amongst homes and commercial areas, where complaints from residents over permanent or rented honey bee colonies have prompted concerns and conflicts.

In view of these mounting problems, investigators and users have attempted to develop alternatives to the honey bee for pollinating crops. For instance, in recent years bumble bees have been increasingly used in the pollination of greenhouse tomatoes and other greenhouse crops. Solitary bees have also shown promise as alternative pollinators. One of these, the alfalfa leafcutting bee, *Megachile rotundata,* has been used for years in the production and growing of alfalfa seed. In 1990, 2.2 billion alfalfa leaf cutting bees, worth nearly $11 million, were used in the U.S. to pollinate alfalfa seed production acreage. In 1976, Phil Torchio at the USDA Agricultural Research Service, Bee Biology Systematics Laboratory in Logan, Utah, initiated investigations into the use of the blue orchard bee, *Osmia lignaria* (also known as the orchard mason bee). The use of these and other solitary bees as pollinators have been reviewed by Jesiolowski (1996, *Organic Gardening,* May/June, pp. 28–35) and Schuessler (1998, *Frontier Magazine,* September/October, pp. 20–23).

Solitary bees have demonstrated several highly desirable characteristics and advantages over honey bees which make them advantageous for use as pollinators on several crops. Most notably, the solitary bees are more efficient pollinators of many crops than honey bees, requiring far fewer bees to pollinate a field or orchard than honey bees. Moreover, some solitary bees are typically active in early spring, often before honey bees reach their optimum activity. For instance, the blue orchard bee will fly at temperatures about 5° lower than honey bees, and will fly more on overcast days and in higher humidity. As such, they are ideal for early spring crops and blossoms which need pollination during the typically poorer weather of this period. Other advantages of note include their gentle nature, and their insusceptibility to the parasites that have recently decimated honey bee populations. Moreover, solitary bees cannot hybridize with African or Africanized honey bees.

Efforts to introduce and rear these solitary bees in orchards and fields have typically involved the provision of nesting blocks in which the bees will nest and lay eggs. Most common nesting blocks are simply formed from blocks of wood into which small holes have been drilled into one face thereof, and into which paper straws may be optionally inserted. Alternatively, nesting blocks are formed from clusters of conventional drinking straws packed into a container with one end left exposed (see Jesiolowski, ibid). However, wooden nesting blocks tend to be difficult to disinfect and are heavy and difficult to drill and handle. If these blocks are not properly disinfected, any eggs laid therein will be susceptible to disease.

More recently, McCarthy (U.S. Pat. No. 4,765,007) has disclosed a nesting block for the alfalfa leaf cutter bee which is formed from a block of molded polystyrene having a plurality of holes extending therethrough. These holes are closed on one end by application of a backing sheet onto one face of the block. In all of these designs, a single adult female bee will form cells within the holes or straws, with each cell having a ball of pollen or nectar upon which a single egg is deposited. Adjacent cells within any one hole or straw are separated from one another by partitions formed from mud or plant parts which differ with each species of cavity nesting solitary bee. After nests have been laid and the adult bees have pollinated the area in the vicinity of the block, the blocks may be collected and stored for use in the next year. When placed in the field the following season, adult bees will emerge from the nests and repeat the cycle.

However, despite these advances, the need persists for improved material and techniques for rearing and managing solitary bees before they can be used on an increasing scale as crop pollinators.

SUMMARY OF THE INVENTION

We have now discovered an improved nesting block for the rearing and management of cavity nesting solitary bees used for pollinating crops. The nesting block includes a chamber having at least one substantially flat face and a plurality of tubes which extend from the face into the chamber. The tubes have an opening through the face, while their opposite end is closed. The chamber is formed from an organic polymeric material, a major portion of which is polycarbonate.

In accordance with this discovery, it is an object of this invention to provide an improved nesting block for the rearing and management of cavity nesting solitary bees.

Another object of the invention is to provide a nesting block and method for rearing and managing solitary bees which may be used to augment, or as an alternative to, pollination with honey bees.

Yet another object of the invention is to provide a nesting block and method for rearing and managing solitary bees which pollinate selected crops with greater efficacy than honey bees.

Still another object of the invention is to provide a nesting block and method for rearing and managing solitary bees which exhibit superior traits in comparison to the honey bee, including reduced susceptibility to Varroa and tracheal mites, inability to cross breed with Africanized honey bees, and greatly reduced propensity to sting.

Other objectives and advantages of the invention will become readily apparent from the ensuing description.

DETAILED DESCRIPTION OF THE INVENTION

The nesting block and method of the invention may be used for the rearing and management of a variety of cavity nesting solitary bees effective for pollinating crops. Without being limited thereto, the device is especially suited to the rearing and management of cavity nesting solitary bees of the genera Osmia, Megachile, and Xylocopa, generally referred to as mason bees, leaf cutter bees, and carpenter bees, respectively. Representative examples of species which are preferred for use herein include the blue orchard bee (*O. lignaria*), and the alfalfa leafcutting bee (*M. rotundata*), as well as the horn faced bee (*O. cornifrons*), the sunflower leafcutting bee (*Megachile pugnata*), and the blueberry bees (*O. attriventris* and *O. ribifloris*). As described in greater detail hereinbelow, use with the blue orchard bee is particularly preferred. The blue orchard bee is a common native bee of North America, living and foraging in most of the continental U.S., and is a highly efficient pollinator of many fruit crops, most notably almonds, apples, cherries, pears, and plums.

Figure 1:
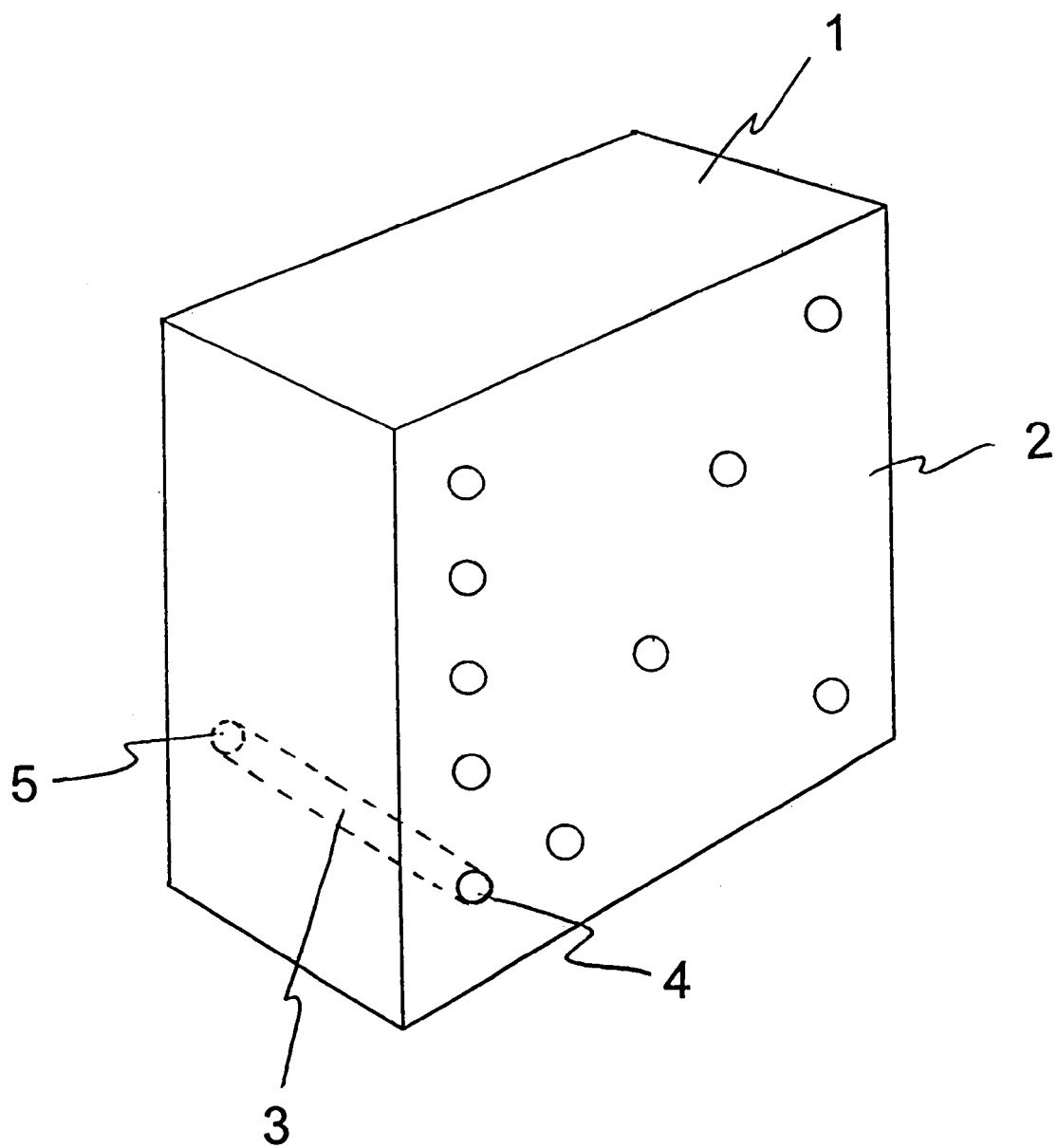
FIG. 1 shows a perspective view of a nesting block of the invention having tubes which are open on one side only.
Figure 2:
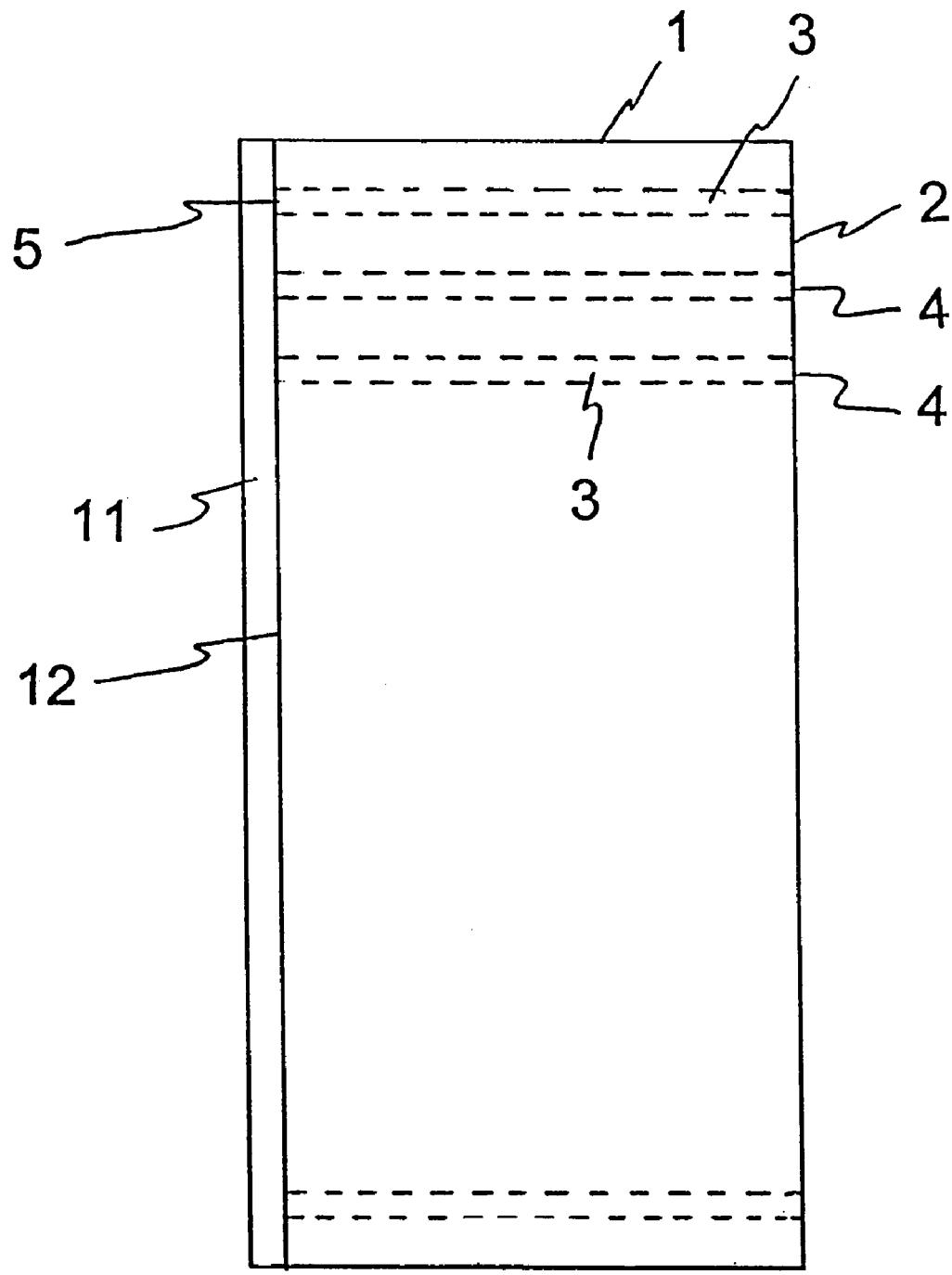
FIG. 2 shows a cross sectional view of an alternative embodiment of the nesting block.
Figure 3:
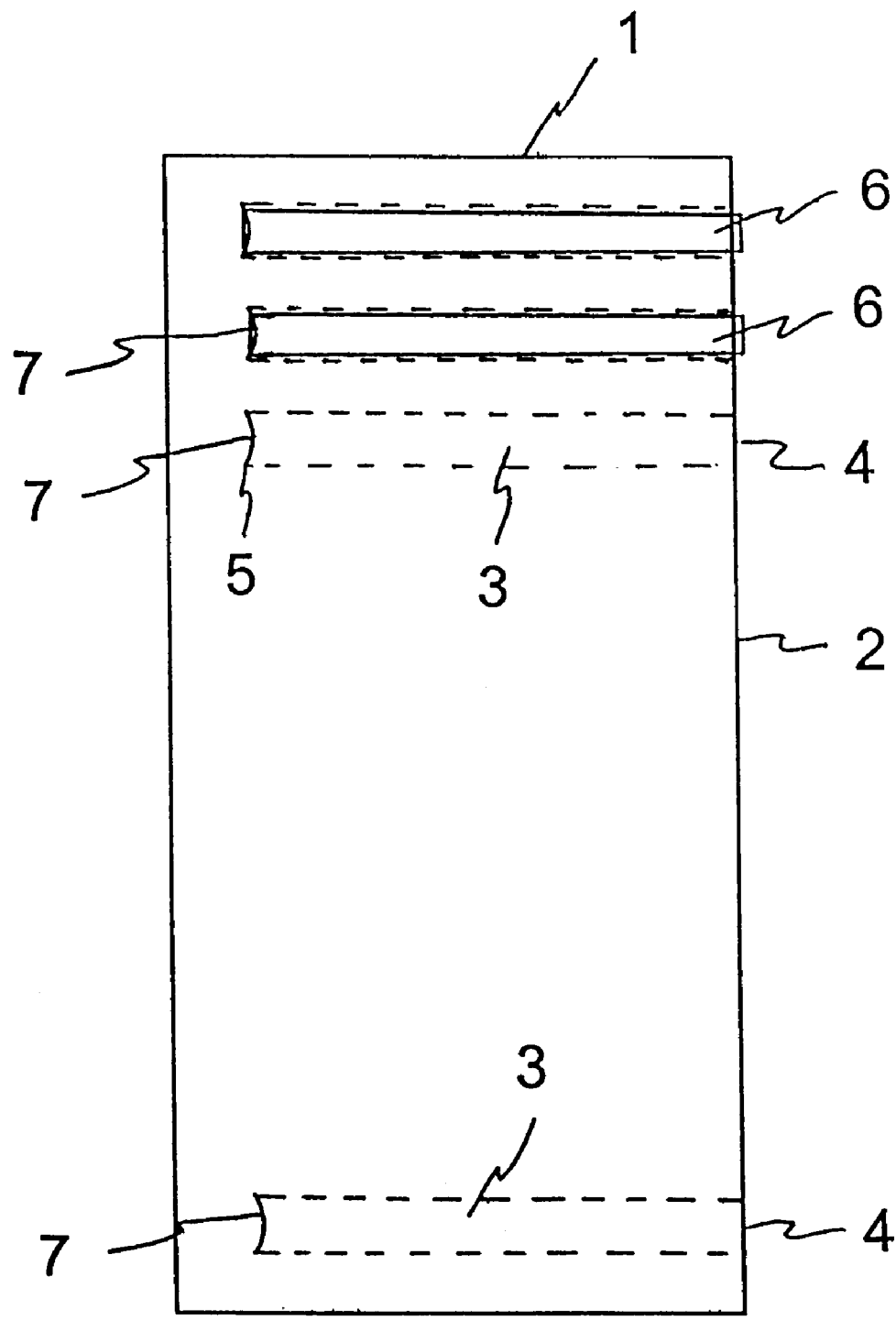
FIG. 3 is a cross sectional view of the nesting block of the invention showing the convex terminus of the tubes.

Referring briefly to FIG. 1, the nesting block of the invention includes a block or chamber 1 with a substantially planar face 2. A plurality of conduits or tubes 3, which have an open end 4 on the face 2, extend into the chamber, providing the nesting cavities in which the bees will construct pollen and nectar provisions and lay their eggs. The opposite end 5 of each of the tubes 3 is closed. In the preferred embodiment, the tubes 3 do not extend completely through the chamber but terminate therewithin. Alternatively, as shown in FIG. 2, tubes 3 may extend through the chamber. In this embodiment, tubes 3 are closed by application of a backing sheet 11 onto the opposite face 12 of the chamber 1. In either embodiment, cylindrical tubes or straws 6 are also preferably inserted within the tubes 3 as shown in FIG. 3. The female bee will then form her cells containing the eggs within the straws. These straws containing the nests, may then be readily removed from the block for handling and for cleaning and disinfection of the block as described in greater detail hereinbelow. However, use of such straws is optional. In a particularly preferred embodiment also shown in FIG. 3, the closed end 5 of the tubes 3 includes a small protrusion 7 extending toward the open end 4.

In accordance with this invention, the chamber 1 of the nesting block is formed from an organic polymer or plastic. The organic polymeric material used in producing the nesting block is critical. We have unexpectedly discovered that by using polycarbonate as the organic polymeric material, the nesting block exhibits superior thermal and moisture properties in comparison to nesting blocks produced from other polymers such as polystyrene, without suffering from the inherent disadvantages of wooden blocks. Nesting blocks produced from polycarbonate as disclosed herein, mimic the thermal properties of wood, resisting heating and cooling relatively quickly after warming such as may typically occur when exposed outdoors on warm, sunny days. Furthermore, nesting blocks formed from polycarbonate exhibit very low water absorption compared to wood, but desirable water vapor transmission (escape) rates which prevent moisture buildup, which would be detrimental to the survival and health of the bees. In addition to these superior moisture and thermal characteristics, nesting blocks constructed from polycarbonate provide the advantages of greater ease of cleaning, disinfection, and handling than possible with conventional nesting blocks. If the nesting block is constructed with a separate backing sheet 11 to close the holes as shown in FIG. 2, the backing sheet may be constructed from any structurally suitable material. However, both the backing sheet and the block 1 are preferably formed from polycarbonate.

Polycarbonates used herein are characterized by the structure:

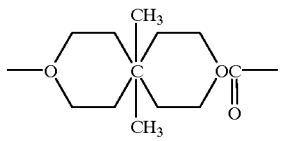

The grade of the polycarbonate used is not critical, and any first generation (virgin) polycarbonate or later generation or recycled polycarbonate (e.g. second, third, fourth generation and so on) are suitable for use herein. As a practical matter, it is expected that the chamber 1 will be constructed from substantially pure polycarbonate. Alternatively, inert fillers may also be mixed or combined with the polymer in forming the chamber 1 of the nesting block to reduce the amount of polycarbonate used and hence reduce costs and weight. However, the skilled practitioner will recognize that any filler must also be extrudable if added to the polymer melt prior to its extrusion. Without being limited thereto, fillers suitable for use herein include wood chips or fibers, and glass fibers, other organic polymers or copolymers, and colored pigments. The amount of any filler will vary with the filler selected and the method of production of the nesting block, and may be readily determined by the skilled practitioner. Typically, suitable amounts of filler will be less than 50% (by weight), preferably less than about 25%, and most preferably less than about 10%. Thus, the major proportion of the organic polymeric material of the chamber is polycarbonate, with a "major proportion" being defined herein as greater than or equal to 50% (by weight). In any event, the amount of any filler should not be so great as to materially affect the desirable thermal and moisture characteristics of the polycarbonate.

The nesting block of the invention may be produced from the polycarbonate using techniques conventional in the art. In accordance with the preferred embodiment, the chamber 1 is produced by molding. The chamber may be molded as a solid block of the polymer or polymer/filler mixture described above, or as a hollow block with the interstitial spaces between the tubes being open. If molded as a hollow block, the thickness of the sides or walls of the tubes should be sufficient to be durable and withstand repeated use and handling. Typically, the wall thickness should be at least about 1/16 to 1/8 inches. Moreover, the interstitial voids between the tubes may be open to the atmosphere, in a sealed vacuum, or optionally contain any suitable inert solid, liquid or gaseous filler. In an alternative embodiment, the nesting block may be made from a solid block or laminated sheets of polycarbonate, and the tubes are formed by drilling holes therein. In another alternative embodiment, the chamber 1 and tubes 3 are not unitary in construction, but may be constructed separately for subsequent assembly. In this embodiment, a hollow chamber 1 may be formed with appropriately sized holes in the face 2 to accommodate the insertion of tubes 3 therein. Protrusions 7 are preferably provided on the interior of the opposite face which are aligned with the holes, to facilitate correct alignment of the inserted tubes. Inserted tubes may be secured by friction fit or suitable adhesive.

Suitable tube size will vary somewhat with the particular bee of interest and may be determined by the practitioner skilled in the art. The cross section of the tube 3 should be of a size and shape effective for allowing passage of the bee therethrough while facilitating construction of nesting cells, while the depth or length of the tube should be sufficient to allow the construction of multiple cells within each tube. Substantially cylindrical tubes having circular cross sections are preferred. When producing the blocks by molding, constructing the tubes with a slight taper, preferably less than about 0.5–1° (in either direction), facilitates the molding process and is therefore preferred. Although it is envisioned that tubes of other various cross-sectional geometries could be used, they may be more difficult to form by molding. Generally, for substantially cylindrical tubes 3, the diameter (internal) will vary between about 4–9 mm while the depth will be greater than or equal to about 8 cm. For use with the blue orchard bee, suitable diameters vary between about 6–9 mm, with diameters between about 7–8 mm being preferred, and the preferred depth is between about 8–16 cm. Applications employing the alfalfa leafcutting or other similar sized solitary bees will typically use slightly smaller diameter tubes, with a diameter of 4–7 mm being suitable, and 5–6 mm being preferred. As with the blue orchard bees, tube depths of greater than about 8 cm are suitable, with depths between about 8–16 cm being preferred. Significantly larger tube diameters may discourage nest building and may be susceptible to invasion by other predatory insects and are thus not preferred.

As described above, the closed end 5 of each of the tubes 3 preferably includes a small protrusion 7 extending toward the open end 4 (FIG. 3). The shape of the protrusion 7 is not critical, but is preferably formed as a substantially convex surface facing the open end 4. Forming the closed end with a protrusion in this manner provides unexpected advantages when using straws 6 inserted within the holes. When using straws in combination with holes having a concave or flat bottomed closed end as is conventional in the art, the female bee may construct the cell containing the first laid egg at the very end of the straw or overhanging the end if the closed end is concave. Upon removal of the straw, this first cell may then be lost or damaged, and nesting material may remain in the hole which is difficult to remove for effective cleaning of the block. However, providing the protrusion 7 at the closed end 5 of the holes effectively forces the female bee to construct the first cell inside the straw and spaced from its end. When the straw is later removed the cell is therefore not lost or damaged, and little or no cellular material is left in the hole making it easier to clean and disinfect.

The size and the geometry of the outer shape of the nesting block are not critical. While six-sided blocks having square or rectangular faces are generally preferred for ease of molding and handling in the field, it is envisioned that the faces may take a variety of shapes or polygons, with an attendant increase or decrease in the number of sides of the block. The size is also variable although blocks which can be fitted together in an arrangement of a size similar to existing honey bee supers, either as a single piece or smaller interlocking blocks which are joined together, are preferred. For example, in one preferred embodiment, four modular blocks having the dimensions, 6.25" deep×10" wide×8.125" high (face 2 having dimensions of 10"×8.125") may be linked together to form a single block 6.25" deep×20" wide×16.25" high, approximately the size of a honey bee super.

Figure 4:
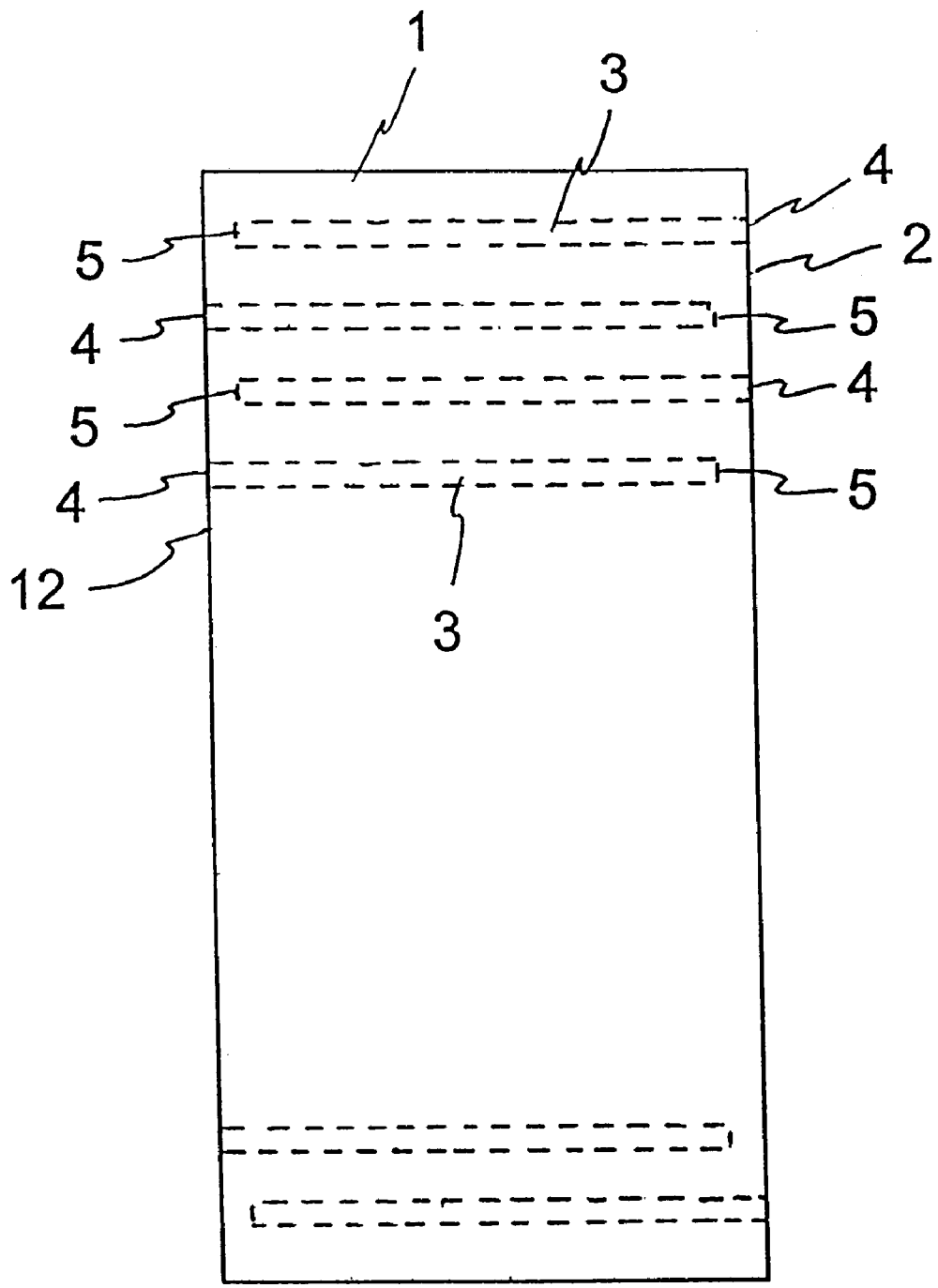
FIG. 4 is a cross sectional view of a preferred embodiment wherein a rectangular nesting block is provided with tubes extending from, and open on, two opposite faces.

Similarly, the number of tubes in the chambers of the blocks is not critical, but will vary with the size of the chamber, the number of faces, and tube spacing. However, because it is recommended that the open ends of the tubes, and hence any faces which have the open ends of the tubes therein, should be exposed to direct sunlight, tubes will typically be extended from fewer than all sides of the chamber. For example, in the preferred embodiment shown in FIG. 4, in a rectangular chamber the tubes are provided extending from only two opposite sides or faces 2 and 12 of the chamber such that one side may be placed facing east to receive morning sunlight, while the opposite side may be positioned facing west where it will receive afternoon sunlight. In the preferred 6.25"×10"×8.125' chambers mentioned above, approximately 50 tubes are provided on (extending from) both of the faces. The tubes from opposed sides are offset from one another, such that the tubes from one side extend between the tubes of the other side without intersecting.

Figure 5:
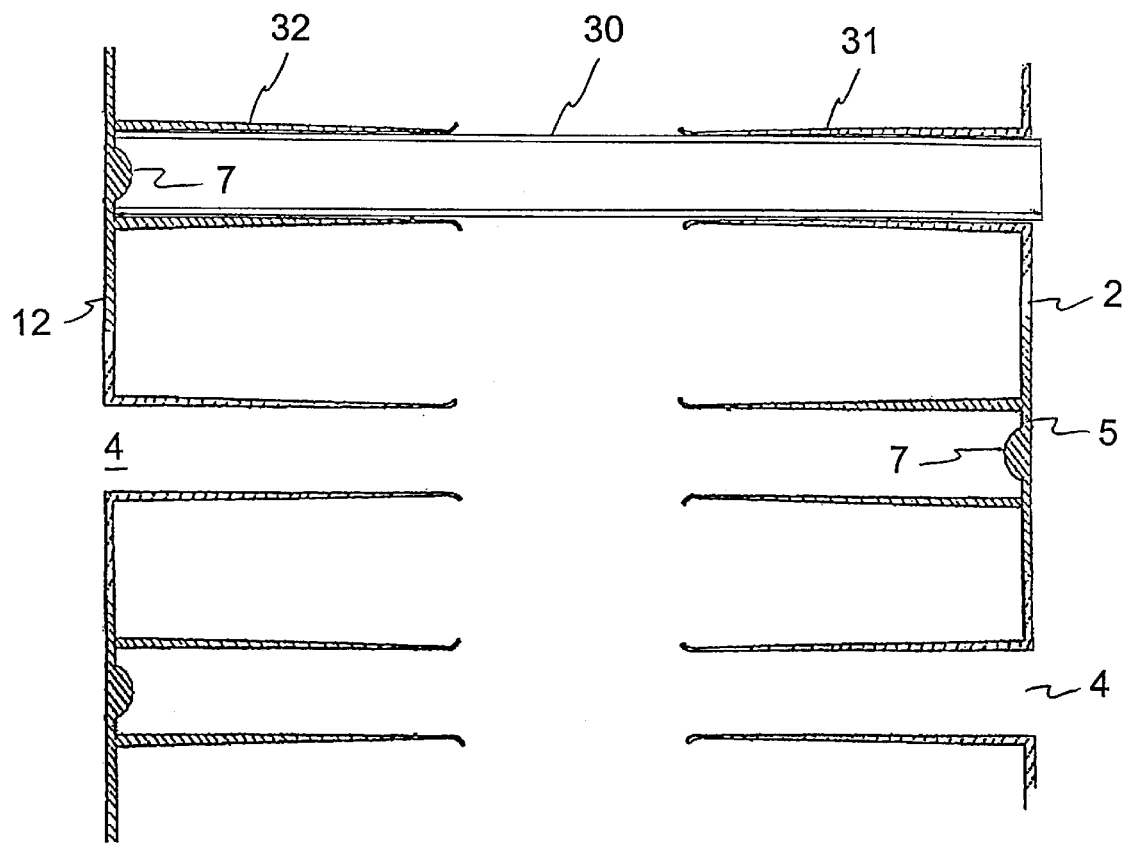
FIG. 5 shows an alternate embodiment of the nesting block of the invention.

In an alternative embodiment shown in FIG. 5, the tubes may be discontinuous or incomplete, lacking a central portion thereof which is intermediate between the open end 4 and closed end 5. Second, discrete tubes 30 may. then be inserted through each open end, extending through the chamber to the closed end, to provide the nesting sites as described above. In this embodiment, the opposed ends of the tube 3 are shown as aligned (coaxial) first and second tube segments or extensions 31 and 32 which extend from the open end 4 and closed end 5, respectively, toward one another in the interior of the chamber 1, but which are not adjoining. Production molding of such nesting blocks having discontinuous tubes may be conducted at lower pressures than required for molding nesting blocks having continuous tubes (e.g., as shown in FIG. 1), thereby reducing the cost for nesting block molds. In use, a substantially straight second tube 30 is inserted through the open end 4 and first tube segment 31, and into the second tube segment 32 abutting the closed end 5. As described hereinabove, protrusions 7 are preferably provided on the closed end 5 so as to project slightly into the tube 30. The tube 30 may be a single walled tube or two or more nested coaxial tubes 33 and 34 as shown in FIG. 6.

The second tube 30, or one or both of the nested tubes 33 or 34, are preferably constructed of a material of sufficient strength to prevent any solitary bee parasitoids from chewing through any one tube 30 and into nests contained within other tubes 30 in the same chamber 1. A variety of materials are suitable for use herein, including plastic, polycarbonate, and cardboard. When using nested tubes, the outer tube 34 is preferably formed from the parasitoid resistant material, allowing inexpensive thin-walled tubes or paper straws to be used for the inner tube 33. The depth and internal diameter of the second tube 30 (or of the innermost tube 33 when using nested tubes) should be the same as those of the continuous tubes 3 disclosed in the embodiments described hereinabove. The wall diameter will vary with the particular material selected, and may be readily determined by the skilled practitioner. Without being limited thereto, cardboard wall thicknesses of between about 1–2 mm are generally sufficient, while suitable walls for plastic tubes may be thinner. The internal diameters of the tube segments 31 and 32 must necessarily be sized to accommodate the insertion of the second tube 30 (or the outer tube 34, if present), and thus may be slightly larger than those of the continuous tubes 3 disclosed in the embodiments described hereinabove, typically between 0–4 mm larger (for cylindrical tube segments). To facilitate the insertion of the second tubes 30 into the tube segments, the innermost ends 35 of the tube segments, particularly the second tube segment 32 extending from the closed end, are outwardly flared or frustroconical in shape.

Figure 6:
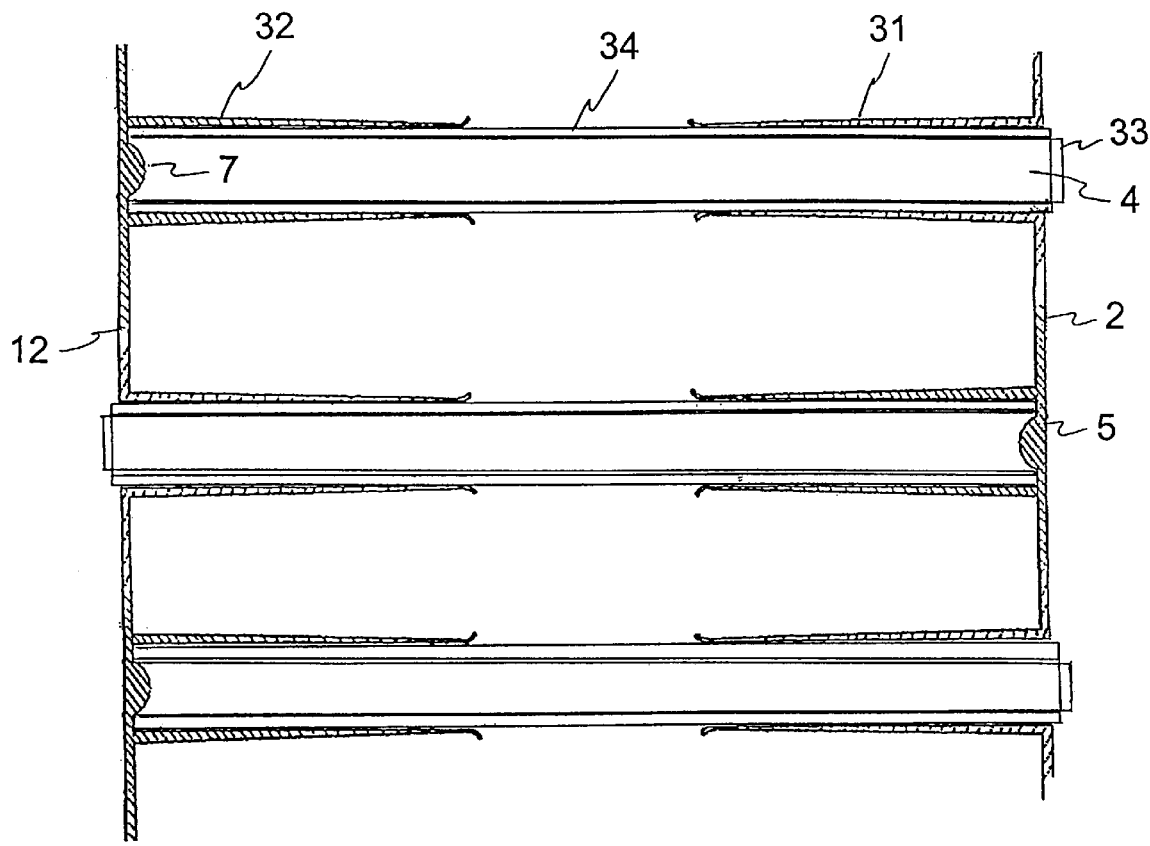
FIG. 6 shows the use of nested tubes inserted into the nesting block of FIG. 5. The length of the tubes has been exaggerated to facilitate illustration.

As also shown in FIGS. 5 and 6, in a preferred configuration of this alternative embodiment, the chamber is provided with tubes extending from two opposite and substantially coplanar faces 2 and 12. Those tubes (and their corresponding aligned tube segments) which are open on one face, are offset from and do not intersect those tubes which are open on the opposed face. The inner surface of any one face will include both first tube segments 31 with an open end 4 into which second tubes 30 may be inserted, as well as second tube segments 32 with a closed end 5 for receiving second tubes 30 inserted through the opposite face. In a particularly preferred embodiment, the chamber is formed from two identical, symmetric halves, each containing alternating tube segments 31 and 32, thereby allowing each half to be constructed from the same mold. The nesting block chamber may then be assembled from any two halves by aligning any first tube segment 31 having an open end 4 on one half, with a second tube segment 32 having a closed end 5 on the second half, and then securing the two halves together.

The cavity nesting solitary bees described above are effective for pollinating many flowering fruits or vegetables that require insect pollination, including the movement of appropriate and viable pollen, as is known in the art. The specific bee to be used may be selected by the skilled practitioner and will vary with the target crop of interest. By way of example, solitary bees which are preferred for use with several crops of particular interest include, but are not limited to:

| Crop | Solitary Bee |
| --- | --- |
| alfalfa | alfalfa leafcutting bee |
| almonds | blue orchard bee |
| apples | blue orchard bee, horn faced bee |
| blueberries | blueberry bees |
| cherries | blue orchard bee |
| pears | blue orchard bee |
| plums | blue orchard bee |
| tomatoes | carpenter bees. |

A more thorough description of crops which may be pollinated by solitary bees are described by Bosch and Kemp [1999, *Bee World,* 80 (4): 163–173], Torchio (1990, Environmental Entomology, 19:1649–1656), Jesiolowski (ibid), Schuessler (ibid), Smith-Heavenrich (1998, *Maine Organic Farmer & Gardener,* March/May, pp. 16–17), Delaplane, ( 1994, *American Bee Journal, January, pp.* 21–22), Henkes (1997, *The Furrow,* November, pp. 10–13), and Wright (1997, *National Gardening,* May/June, pp. 32–37, 74), the contents of each of which are incorporated by reference herein.

In use, the nesting block is placed in the vicinity or locus of the orchard or field containing the crops to be pollinated shortly before the adult bees are to emerge and the crops are to be pollinated. The blocks will be positioned with the faces and tube openings directed toward the east or west to receive sunlight. In the preferred embodiment, straws 6 are inserted into the tubes 3 abutting the closed end 5 with the opposite end extending to or slightly beyond the face at the opening 4. The straws may be constructed of a wide variety of materials, although cardboard tubes or paper "soda straws" are inexpensive and readily available and are therefore typically preferred. The diameter of the straws is selected to readily slide into the tubes while the length should be substantially the same as, or slightly longer than the holes 3.

Figure 7:
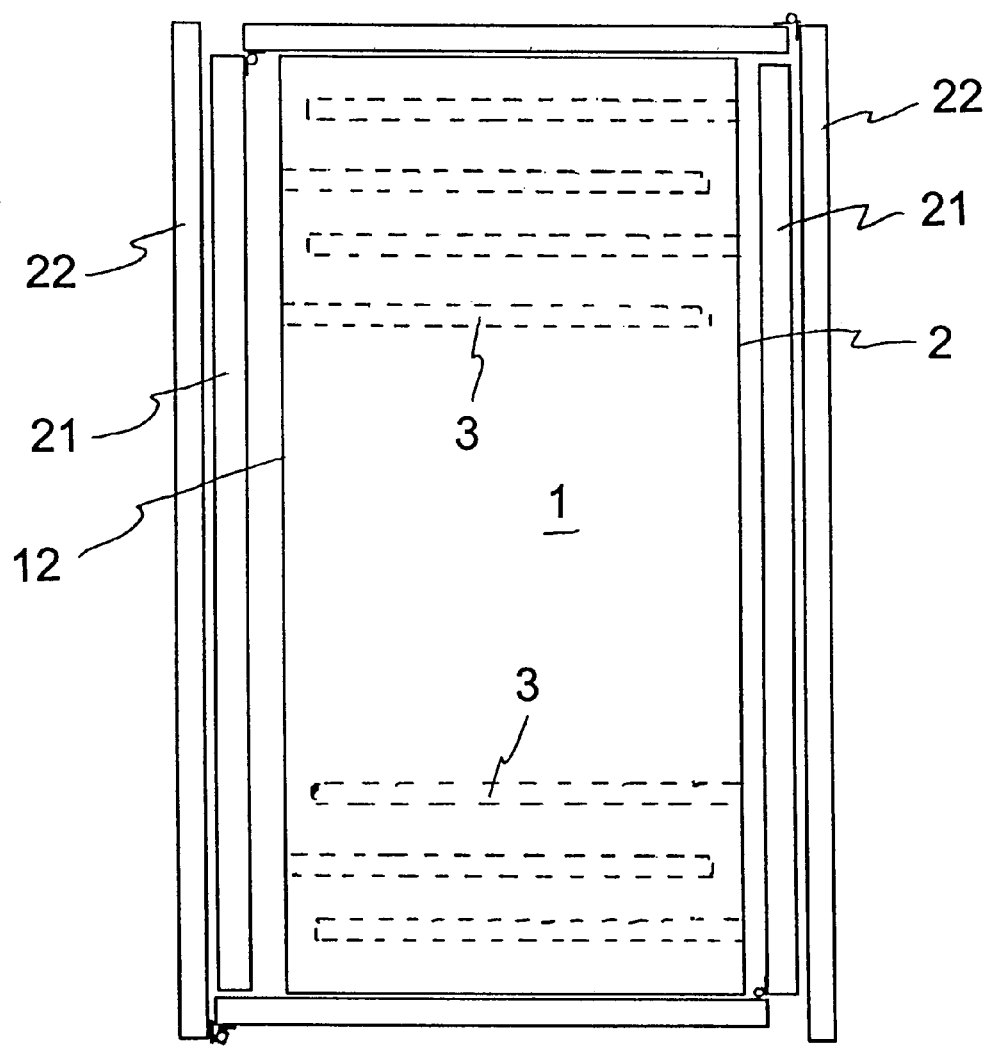
FIG. 7 shows the nesting block of the invention in combination with an optional lattice and cover, for easy transportation and deployment.

Although the blocks may be used in the field "as is", a lattice or mesh screen 21 and/or hinged cover or locator board 22 may also be provided over the faces containing the tube openings as shown in FIG. 7. The lattices and cover boards may be constructed in a similar manner to honey bee supers which are well known in the art. Indeed, depending upon the size and shape of the nesting block, it may even be placed in existing honey bee supers. To protect the nests from rain and any agricultural chemicals which may be applied to the surrounding crops, the block may also be placed under protection of an overhang, roof or other cover. Adult female solitary bees, either wild or which have emerged from preexisting nests in the same or other nesting block (see below), will form new nests in the empty holes or straws of the nesting block early in the season and generally concurrently with pollination of the nearby crops. While the blocks may be left in the field until the following season, the eggs in the nests may be susceptible to predatory insects, disease, and climactic extremes. Therefore, in the preferred embodiment the completed nests and possibly the blocks are collected and removed from the field shortly after the females have finished constructing the nests and are placed into storage. Moreover, the timing of the emergence of the bees the following season may be controlled by storage under appropriate temperatures.

Nesting blocks containing the nests may be immediately stored. In a particularly preferred embodiment, the blocks are first stored at room temperature in a dark room under black lights with mineral oil trays therein for a short period of time, usually throughout the summer, to attract and kill any parasitoids which may otherwise attack the bee nests. The blocks may then be stored (wintered) at approximately 2–5° C. until such time as the blocks will be readied for use in the upcoming season. Typically, the blocks will be stored for approximately 180–230 days depending upon the date needed for pollination. Immediately prior to use, the blocks are removed from refrigeration, the straws are removed from the blocks, and the blocks are cleaned and sterilized. After this cleaning, a portion of the straws containing nests, preferably about 10%, are returned into the same nesting block while clean straws are inserted into the unoccupied holes. The remaining straws containing nests which have been removed from the block are distributed between fresh nesting blocks, again leaving many of the holes therein unoccupied. These blocks are then placed out in the orchard or field to repeat the cycle. Moreover, by distributing the pre-existing nests between an increased number of blocks with many open holes, a greater number of holes are provided for laying of the next generation of eggs, providing a significantly increased population of bees each successive year.

The precise time of use, including the placement of the blocks in the field and their recovery, will vary with the latitude, crop and specific bee of interest and may be readily determined by the user. For instance, when pollinating with the blue orchard bee for cherries in Utah, the blocks should be positioned in the field in March, while for almonds in California, the blocks should be placed in the field in late January or February. The blocks are then collected approximately 2–3 months after their positioning in the field.

It is understood that the foregoing detailed description is given merely by way of illustration, and that modifications and variations may be made therein without departing from the spirit and scope of the invention.

We claim:

1. A nesting block for cavity nesting solitary pollinating bees comprising a chamber constructed from material comprising an organic polymer component and wherein a major proportion of said organic polymer component is polycarbonate, said chamber comprising a first substantially flat face, and a plurality of tubes extending into said chamber from said face, said tubes having an open end through said first face and a closed opposite end, said tubes having a cross section effective for allowing passage of said bees therethrough and construction of nests therein by said bees.

2. The nesting block of claim 1 wherein said tubes terminate within the interior of said chamber.

3. The nesting block of claim 1 wherein the closed end of said tubes comprises a protrusion extending toward said face.

4. The nesting block of claim 3 wherein said tubes terminate within the interior of said chamber and said protrusion comprises a substantially convex surface.

5. The nesting block of claim 1 wherein said organic polymer component consists essentially of polycarbonate.

6. The nesting block of claim 1 wherein said material from which said chamber is constructed comprises said organic polymer component in combination with an inert filler.

7. The nesting block of claim 6 wherein said inert filler is selected from the group consisting of wood, glass fibers, non-polycarbonate organic polymers, and copolymers.

8. The nesting block of claim 1 wherein said material from which said chamber is constructed comprises said organic polymer component in combination with a colored pigment.

9. The nesting block of claim 8 wherein the substantially cylindrical sides of said tubes are tapered between approximately 0.5–1.0°.

10. The nesting block of claim 1 wherein said tubes comprise continuous walls extending between said open end and said closed end.

11. The nesting block of claim 1 wherein said tubes are substantially cylindrical.

12. The nesting block of claim 11 wherein the diameter of said tubes is between approximately 4–9 mm.

13. The nesting block of claim 12 wherein the diameter of said tubes is between approximately 6–9 mm.

14. The nesting block of claim 13 wherein the diameter of said tubes is between approximately 7–8 mm.

15. The nesting block of claim 12 wherein the diameter of said holes is between approximately 5–6 mm.

16. The nesting block of claim 11 wherein the depth of said tubes is greater than or equal to approximately 8 cm.

17. The nesting block of claim 16 wherein the depth of said tubes is between approximately 8–16 cm.

18. The nesting block of claim 11 wherein the distance between said open end of a first tube segment and said closed end of a second tube segment aligned and coaxial with said first tube segment is greater than or equal to approximately 8 cm.

19. The nesting block of claim 18 wherein said distance is between approximately 8–16 cm.

20. The nesting block of claim 1 wherein said chamber comprises interstitial void spaces between said tubes.

21. The nesting block of claim 20 wherein said chamber further comprises an inert filler within said interstitial void spaces.

22. The nesting block of claim 21 wherein said inert filler is selected from the group consisting of air, gas, and wood.

23. The nesting block of claim 1 wherein said chamber has two of said substantially flat faces, said faces being on opposing sides of said chambers, and each of said faces having a plurality of said tubes extending into said block.

24. The nesting block of claim 23 wherein said tubes on said opposing sides of said block are offset from one another.

25. The nesting block of claim 1 wherein said chamber is constructed from a single molded piece of said material comprising said organic polymer component.

26. The nesting block of claim 1 wherein said chamber is formed from laminated sheets of said material comprising said organic polymer component.

27. A nesting block for cavity nesting solitary pollinating bees comprising a chamber constructed from material comprising an organic polymer component and wherein a major proportion of said organic polymer component is polycarbonate, said chamber comprising first and second faces on opposite sides thereof, at least said first face being substantially flat, first tube segments extending into said chamber from said first face, said first tube segments having an open end through said first face, and second tube segments extending into said chamber from said second face toward said first face, said second tube segments having a closed end adjacent to said second face, said first and second tube segments being aligned and coaxial such that a straight tube may be inserted through said first tube segment into said second tube segment and abut said closed end, wherein said tube segments have a cross section effective for allowing passage of said bees therethrough.

28. The nesting block of claim 27 wherein said closed end of said second tube segments comprises a protrusion extending toward said first face.

29. The nesting block of claim 28 wherein said protrusion comprises a substantially convex surface.

30. The nesting block of claim 27 wherein said organic polymer component consists essentially of polycarbonate.

31. The nesting block of claim 27 wherein said material from which said chamber is constructed comprises said organic polymer component in combination with an inert filler.

32. The nesting block of claim 31 wherein said inert filler is selected from the group consisting of wood, glass fibers, non-polycarbonate organic polymers, and copolymers.

33. The nesting block of claim 27 wherein said material from which said chamber is constructed comprises said organic polymer component in combination with a colored pigment.

34. The nesting block of claim 27 wherein said first and second tube segments are substantially cylindrical.

35. The nesting block of claim 34 wherein the diameter of said tubes is between approximately 4–13 mm.

36. The nesting block of claim 35 wherein the diameter of said tubes is between approximately 6–13 mm.

37. The nesting block of claim 36 wherein the diameter of said tubes is between approximately 7–12 mm.

38. The nesting block of claim 37 wherein the diameter of said holes is between approximately 5–10 mm.

39. The nesting block of claim 27 wherein said second face is substantially flat, and said chamber further comprises third tube segments extending into said chamber from said second face, said third tube segments having an open end through said second face, and fourth tube segments extending into said chamber from said first face toward said second face, said fourth tube segments having a closed end adjacent to said first face, said third and fourth tube segments being aligned and coaxial such that a straight tube may be inserted through said third tube segment into said fourth tube segment and abut said closed end of said fourth tube segment, wherein said third and fourth tube segments have a cross section effective for allowing passage of said bees therethrough.

40. The nesting block of claim 39 wherein said chamber is constructed from two molded pieces of said material comprising said organic polymer component.

* * * * *